United States Patent [19]

Förster

[11] 4,268,249
[45] May 19, 1981

[54] ORTHODONTIC BRACKET AND METHOD OF RETAINING A WIRE THEREIN

[75] Inventor: Rolf Förster, Pforzheim, Fed. Rep. of Germany

[73] Assignee: Bernhard Förster GmbH, Pforzheim, Fed. Rep. of Germany

[21] Appl. No.: 138,219

[22] Filed: Apr. 7, 1980

[30] Foreign Application Priority Data

May 16, 1979 [DE] Fed. Rep. of Germany ...... 2919640

[51] Int. Cl.³ .............................................. A61C 7/00
[52] U.S. Cl. .................................................. 433/10
[58] Field of Search .................... 433/9, 13, 16, 10, 11

[56] References Cited

U.S. PATENT DOCUMENTS 3,946,488  3/1976  Miller et al. ........................ 433/11
4,209,906  7/1980  Fujita ................................... 433/11

Primary Examiner—Robert Peshock
Attorney, Agent, or Firm—Balogh, Osann, Kramer, Dvorak, Genova & Traub

[57] ABSTRACT

The bracket comprises flange means adapted to be secured to a tooth of a patient, a bearing member having a neck portion connected to said flange means and a through hole on an axis which is transversely spaced from said flange means, and a rotary catch member mounted in said through hole for rotation on said axis and defining with said neck portion and said flange means a channel which is disposed on one side of said bearing member and open opposite to said neck portion and adapted to receive a wire so that the latter is engageable with said flange means. The rotary catch member is formed with actuating means which are peripherally spaced from said channel and engageable by an implement for rotating the rotary catch member. The rotary catch member is rotatable on said axis to a retaining position and in said retaining position is adapted to retain a wire in said channel. A U-shaped member is detachably fitted over said neck portion and has a crosspiece extending in said channel. The channel is adapted to receive a square-section wire in engagement with said U-shaped member. The rotary catch member is adapted in said retaining position to retain said square-section wire in said channel and in engagement with said U-shaped member.

5 Claims, 10 Drawing Figures

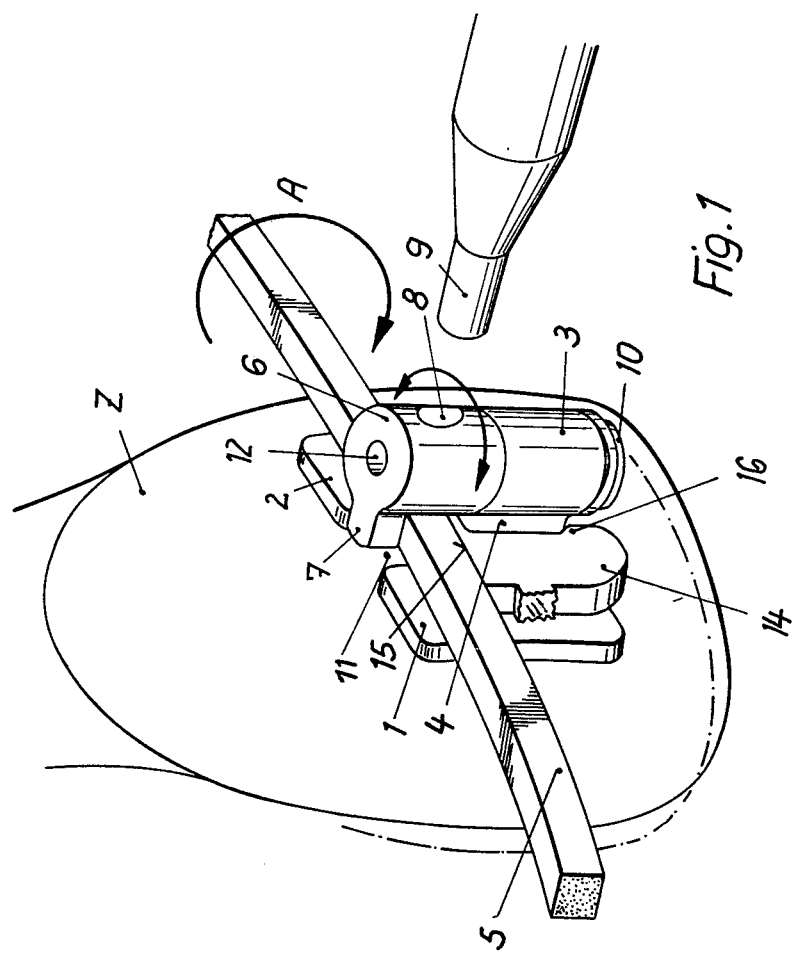

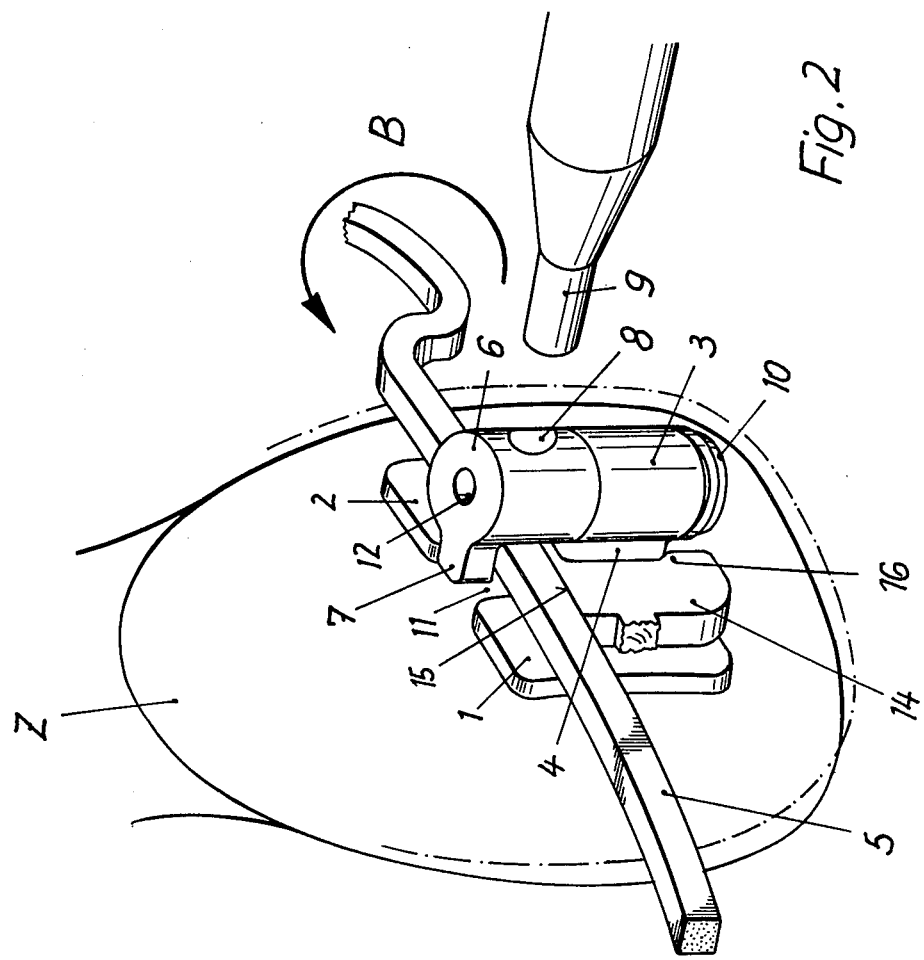

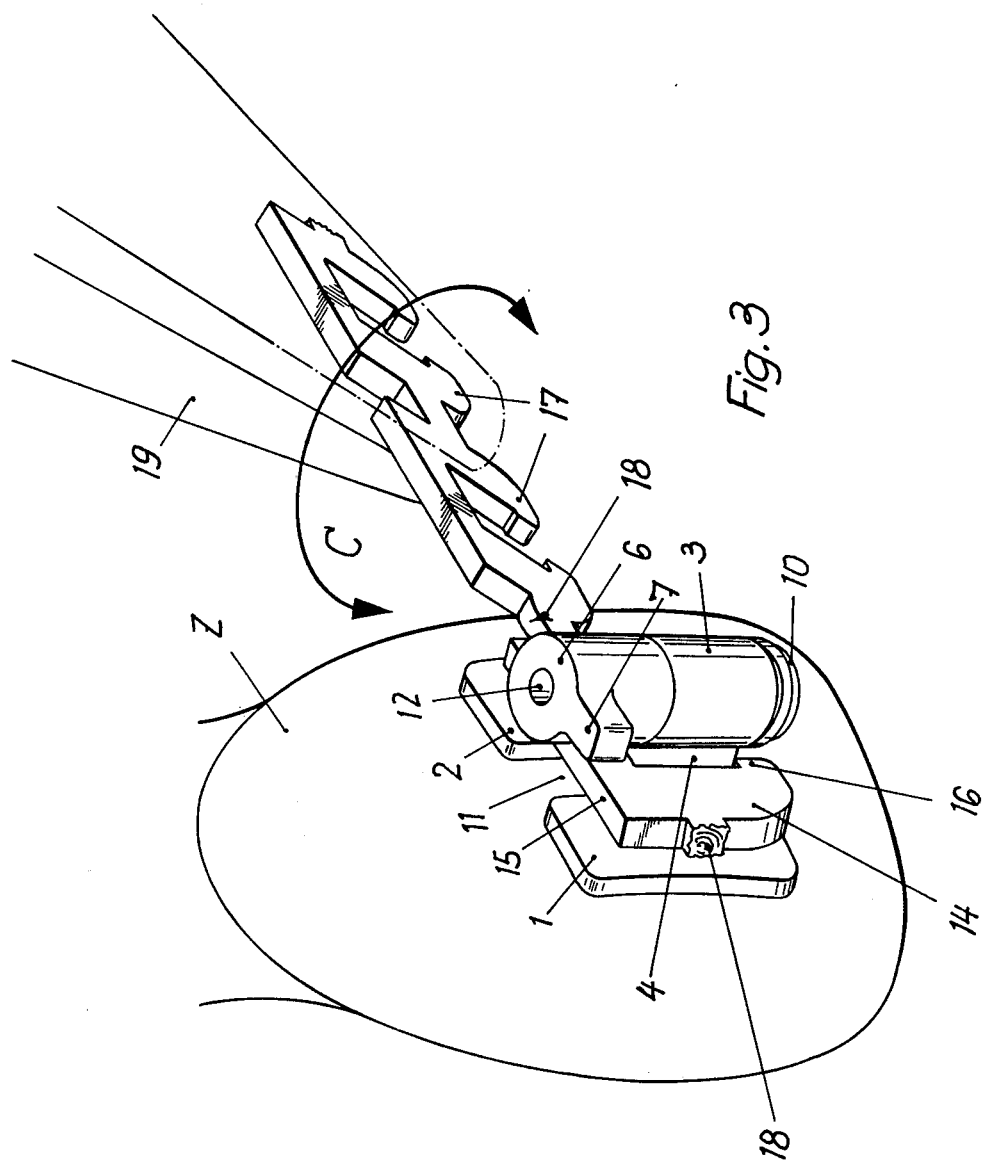

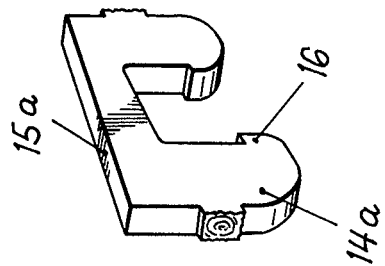
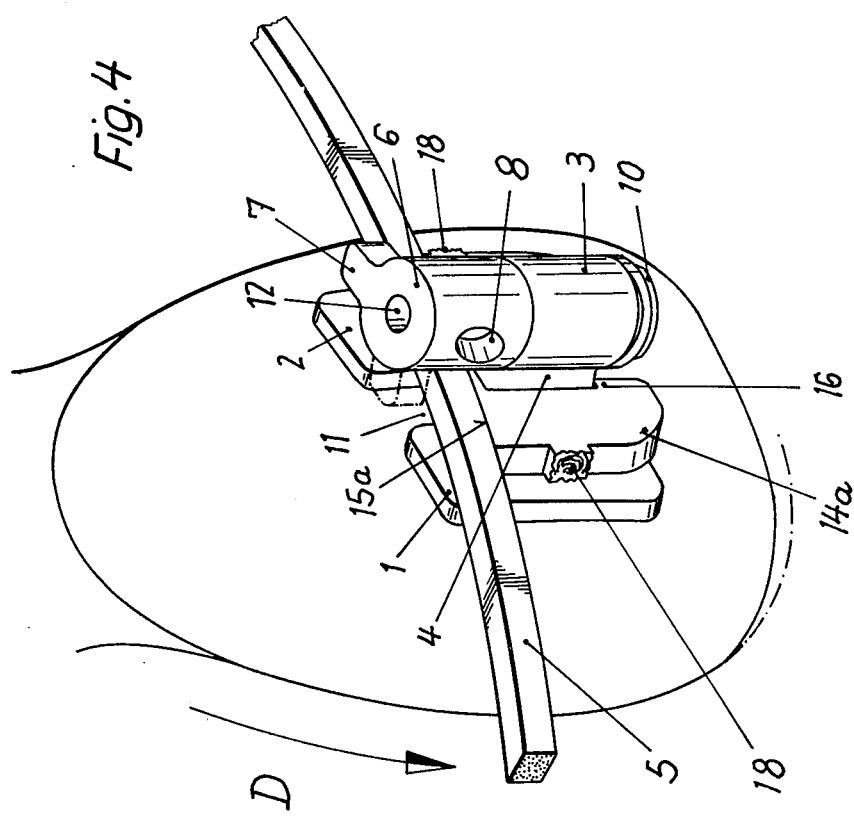

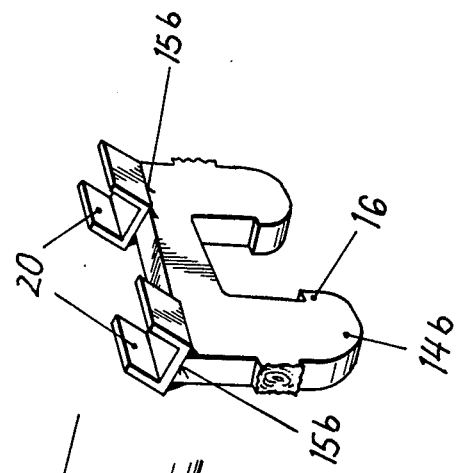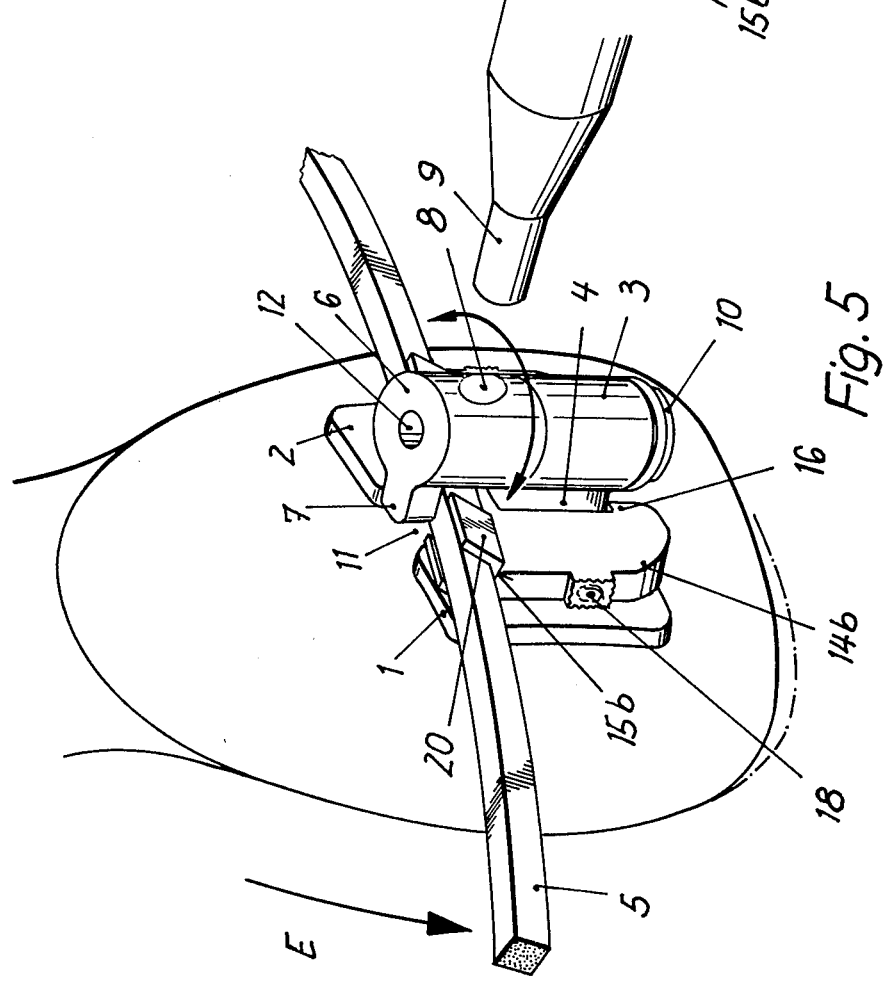

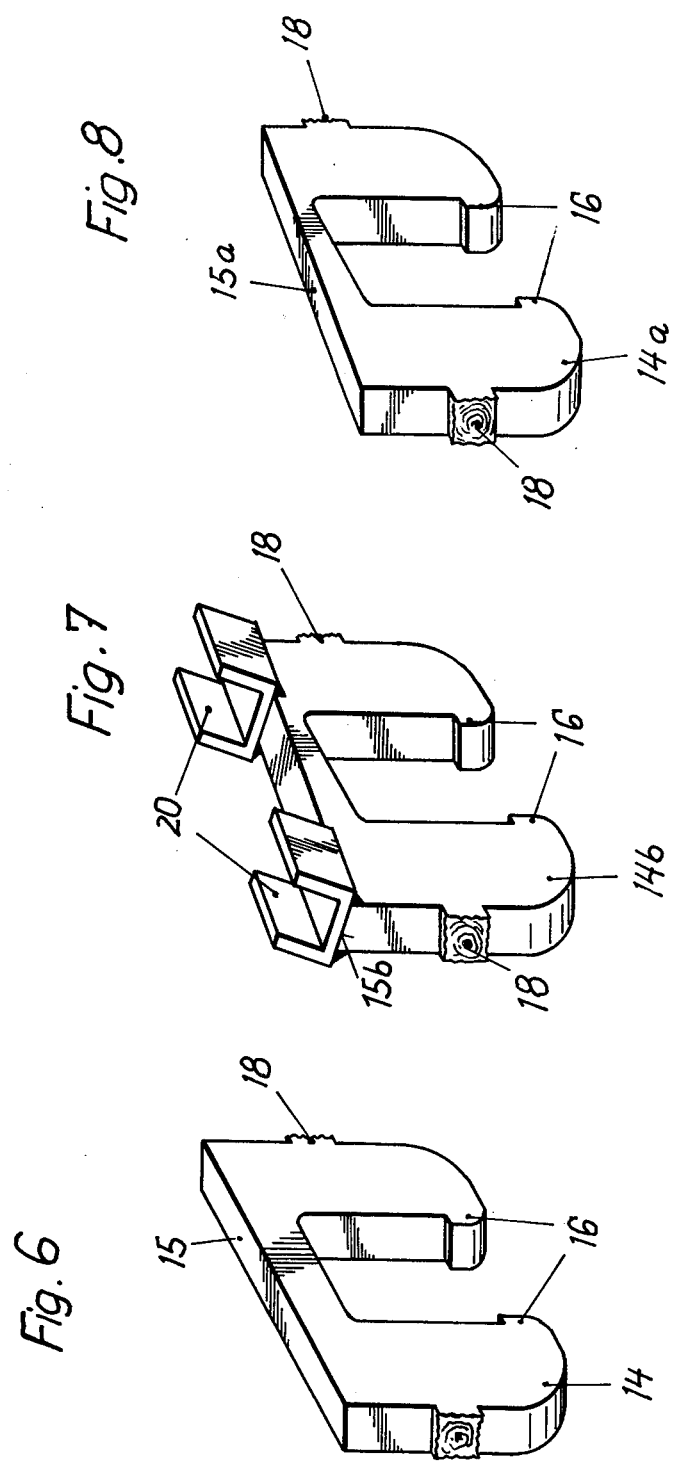

ORTHODONTIC BRACKET AND METHOD OF RETAINING A WIRE THEREIN

This invention relates to an orthodontic bracket, particularly to an improvement of the orthodontic bracket disclosed in U.S. patent application Ser. No. 921,188 (Förster) filed July 3, 1978, now Pat. No. 4,196,517 issued Apr. 8, 1980 which will be referred to hereinafter as the Förster reference. The disclosure of said reference is explicitly incorporated herein by reference.

The orthodontic bracket according to the Förster reference identified above comprises flange means for securing the bracket to a tooth of a patient, a bearing member having a neck portion connected to said flange means and a through hole on an axis which is transversely spaced from said flange means, a rotary catch member mounted in said through hole for rotation on said axis and defining with said neck portion and said flange means a channel, which is disposed on one side of said bearing member and open opposite to said neck portion and adapted to receive a wire so that the latter is engageable with said neck portion. The rotary catch member is formed with a radial blind bore which is peripherally spaced from the side of said rotary catch member facing said channel and engageable by an implement for rotating said rotary catch member. The rotary catch member is rotatable on said axis to a wire-retaining position and in said wire-retaining position is adapted to retain a wire in said channel.

The known bracket can be used for the so-called Begg light-wire technique, which uses a round-section wire and for a successful orthodontic treatment requires that the wire has a certain freedom of movement in the bracket and is adapted to engage the bracket only in point contact. Other known brackets are used for the so-called edgewise technique, in which a square-section wire is used which should contact the bracket over the largest possible distance across the width of the tooth. The square-section wire can be rotated about its own axis in order to exert on the tooth a torque for changing the angle of the generally vertical axis of the tooth.

It is an object of the invention to provide a bracket which can be used for both techniques so that the Begg light-wire technique can be employed first and be followed by the edgewise technique in which a square-section arched wire is used, which contacts the bracket over the largest possible distance across the width of the tooth, such square-section wire can be used to control by means of the bracket the torque exerted on the tooth and the angulation of its axis to effect a very fine adjustment of the occlusion.

This object is accomplished according to the invention in that a U-shaped member is fitted over the neck portion of the bearing member and has a cross-piece for engaging and guiding a square-section wire, which is adapted to be fixed in position by the rotary catch member. For this reason the bracket can be used for the edgewise technique using a square-section wire when the use of the bracket for the technique employing a round-section wire has resulted in an initial correction of a tooth.

Further details of the orthodontic bracket according to the invention will now be explained with reference to the accompanying drawings, in which FIGS. 1 and 2 are perspective views showing the use of a bracket embodying the invention for a correction of teeth according to different techniques, FIG. 3 is a perspective view showing how the bracket is prepared for the uses shown in FIGS. 1 and 2, FIGS. 4 and 5 are perspective views showing the use of brackets according to the invention for other corrections, FIGS. 4a and 5a are perspective views showing the U-shaped members used in the brackets of FIGS. 4 and 5, respectively, and FIGS. 6 to 8 show three embodiments of U-shaped members for the purpose illustrated in FIGS. 1 to 5.

Just as the bracket disclosed in the Förster reference the bracket shown on the drawings comprises two flat flanges 1, 2 or and a bearing member 3, which is disposed between the flanges 1, 2 and has a through hole for rotatably mounting a pin. When the present bracket is used for the edgewise technique, the neck portion 4 of the bearing member 3 is only indirectly engageable by the square-section wire 5 and the lather can be retained by means of a rotary catch member 6 which has been disclosed in the Förster reference. The catch member 6 comprises a pivot pin rotatably mounted in the through hole of the bearing member 3 and a catch nose 7. The body of the rotary catch member 6 is formed with a blind bore 8, which is disposed opposite to the catch nose 7 and adapted to receive an end pin of an implement 9, which can be used to rotate the rotary catch member 6.

Just as in the Förster reference the bearing member 3 and the flange plates 1, 2 form an assembly which is Ω-shaped in cross-section, the rotary catch member 6 is pivotally movable in a plane that is parallel to the flange plates 1, 2 and its catch nose 7 extends into the gap between the flange plates 1, 2. The body of the rotary catch member 6 provided with the catch nose 7 is disposed at one end of the bearing member 3. A disc spring 10 is disposed at the other end of the bearing member 3 and cooperates with the pivot pin of the rotary catch member to urge the body thereof into frictional engagement with the bearing member 3.

Just as is disclosed in the Förster reference, the bearing member 3 is formed in the present embodiment with a longitudinal groove 11, which extends between the two flange plates 1, 2 and is adapted to receive erecting springs, and the bearing member 3 is also formed with through bores 12, for receiving erecting springs. The flange plates 1, 2 may be directly cemented to the tooth Z to be corrected or may be welded to a strap, not shown, which is secured to the tooth.

The bracket disclosed in the Förster reference is used for the Begg light-wire technique, in which a round-section wire is used. The bracket provided according to the invention can be used for the Begg light-wire technique as well as for the edgewise technique using a square-section wire. For the latter use, a U-shaped member 14 is fitted over the neck portion 4 of the bearing eye 3 when the bracket has been secured to the tooth Z. The U-shaped member 14 has a cross-piece 15 for engaging and guiding a square-section wire 5, which can subsequently be fixed in position by the rotary catch member 7, as is shown in FIGS. 1 and 2. The square-section wire 5 can then be used to exert a torque on the bracket in the senses indicated by arrows A and B in FIGS. 1 and 2, respectively. The U-shaped member 14 is provided at the ends of its legs with inwardly protruding noses 16, which snap in behind the neck portion 4 as the U-shaped member 14 is fitted thereon.

FIG. 3 illustrates the fitting of a U-shaped member 14 which is part of a strip 17 consisting of a series of such U-shaped members 14. When the U-shaped member 14 has been fitted on the neck portion 4, the strip 17 is twisted by means of pliers 19 so that the U-shaped member 14 breaks off at the notch 18. This is a very convenient manner of fitting the U-shaped member 14 on the bracket 1 to 12 which has been fixed to the tooth and has already been used for a correction by the Begg light-wire technique. At the end opposite to the U-shaped member 14 to be fitted on the bracket, the strip 17 may be provided with a handle, which is not shown here.

FIG. 4 shows bracket 1 to 12 provided with a U-shaped member 14a in which the upper surface of the cross-piece 15a is longitudinally inclined to impart to the tooth a predetermined angulation in the sense indicated by the arrow D.

FIG. 5 shows a bracket 1 to 12 provided with a U-shaped member 14b in which the upper surface of the crosspiece 15b is transversely inclined and has oblique guide elements 20 secured to it, which serve to receive and guide a square-section wire 5 for exerting a torque in the senses indicated by the arrow E.

The U-shaped members 14a and 14b used in accordance with FIGS. 4 and 5 are separately shown in FIGS. 4a and 5a, respectively.

FIGS. 6 to 8 are perspective views showing a U-shaped member 14 provided with a crosspiece 15 (FIG. 6), a U-shaped member 14a having a crosspiece 15a with a longitudinal inclined upper surface, and a U-shaped member 14b having a crosspiece 15b with a transversely inclined upper surface, to which oblique wire guides 20 are secured. A square-section wire 5 used to correct a tooth in accordance with FIGS. 1 to 5 can be guided by the upper surface of the crosspieces 15 or 15a and can be received and guided by the oblique wire guides 20. The detent noses 16 and the portions 18 where the U-shaped members have been broken off at the notches are also apparent from FIGS. 6 to 8.

What is claimed is:

1. In an orthodontic bracket comprising flange means adapted to be secured to a tooth of a patient, a bearing member having a neck portion connected to said flange means and a through hole on an axis which is transversely spaced from said flange means, and a rotary catch member mounted in said through hole for rotation on said axis and defining with said neck portion and said flange means a channel which is disposed on one side of said bearing member and open opposite to said neck portion and adapted to receive a wire so that the latter is engageable with said flange means, said rotary catch member being formed with actuating means which are peripherally spaced from said channel and engageable by an implement for rotating said rotary catch member, said rotary catch member being rotatable on said axis to a retaining position and in said retaining position being adapted to retain a wire in said channel, the improvement residing in that a U-shaped member is detachably fitted over said neck portion and has a crosspiece extending in said channel, said channel is adapted to receive a square-section wire in engagement with said U-shaped member, and said rotary catch member is adapted in said retaining position to retain said square-sectionwire in said channel and in engagement with said U-shaped member.

2. The improvement set forth in claim 1, in which said actuating means define in said rotary catch member a blind bore for receiving said implement.

3. The improvement set forth in claim 1, in which said U-shaped member comprises two legs which extend from said crosspiece on opposite sides of said neck portion and are formed with inwardly protruding noses engaging said neck portion on the side opposite to said crosspiece.

4. The improvement set forth in claim 1, in which said crosspiece has on the side opposite to said neck portion a longitudinally inclined surface.

5. The improvement set forth in claim 1, in which wire guides for receiving said square-section wire are secured to said crosspiece on the side thereof opposite to said neck portion and are disposed on opposite sides of said rotary catch member and inclined relative to said axis.

* * * * *